(12) United States Patent
Johnson et al.

(10) Patent No.: US 9,446,961 B2
(45) Date of Patent: Sep. 20, 2016

(54) MCM-56 MANUFACTURE

(75) Inventors: Ivy D. Johnson, Lawrenceville, NJ (US); Nadya A. Hrycenko, Clinton, NJ (US); Wieslaw J. Roth, Sewell, NJ (US); Terry E. Helton, Bethlehem, PA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 330 days.

(21) Appl. No.: 14/238,274

(22) PCT Filed: Aug. 16, 2012

(86) PCT No.: PCT/US2012/051181
§ 371 (c)(1),
(2), (4) Date: Apr. 23, 2014

(87) PCT Pub. No.: WO2013/048636
PCT Pub. Date: Apr. 4, 2013

(65) Prior Publication Data
US 2014/0234207 A1    Aug. 21, 2014

Related U.S. Application Data

(60) Provisional application No. 61/535,632, filed on Sep. 16, 2011.

(30) Foreign Application Priority Data

Nov. 10, 2011 (EP) .................................. 11188529

(51) Int. Cl.
| | | |
|---|---|---|
| *C01B 39/48* | (2006.01) | |
| *B01J 29/70* | (2006.01) | |
| *B01J 29/74* | (2006.01) | |
| *B01J 29/76* | (2006.01) | |
| *B01J 29/78* | (2006.01) | |
| *C07C 2/66* | (2006.01) | |

(52) U.S. Cl.
CPC ................ *C01B 39/48* (2013.01); *B01J 29/70* (2013.01); *B01J 29/74* (2013.01); *B01J 29/76* (2013.01); *B01J 29/78* (2013.01); *C07C 2/66* (2013.01); *B01J 2229/186* (2013.01); *B01J 2229/42* (2013.01); *C07C 2529/70* (2013.01); *Y02P 20/52* (2015.11)

(58) Field of Classification Search
CPC ......... C01B 39/48; B01J 29/70; B01J 29/74; B01J 29/78; B01J 2229/42; B01J 2229/186
See application file for complete search history.

(56) References Cited

U.S. PATENT DOCUMENTS

| | | |
|---|---|---|
| 3,308,069 A | 3/1967 | Wadlinger et al. |
| 3,449,070 A | 6/1969 | McDaniel et al. |
| 3,751,504 A | 8/1973 | Keown, et al. |
| 3,766,093 A | 10/1973 | Chu |
| 3,894,104 A | 7/1975 | Chang et al. |
| 4,016,218 A | 4/1977 | Haag et al. |
| 4,415,438 A | 11/1983 | Dean et al. |
| 4,439,409 A | 3/1984 | Puppe et al. |
| 4,547,605 A | 10/1985 | Kresge et al. |
| 4,826,667 A | 5/1989 | Zones et al. |
| 4,891,458 A | 1/1990 | Innes et al. |
| 4,954,325 A | 9/1990 | Rubin et al. |
| 4,992,606 A | 2/1991 | Kushnerick et al. |
| 5,236,575 A | 8/1993 | Bennett et al. |
| 5,250,277 A | 10/1993 | Kresge et al. |
| 5,334,795 A | 8/1994 | Chu et al. |
| 5,362,697 A * | 11/1994 | Fung ........................ B01J 29/70 423/718 |
| 5,453,554 A | 9/1995 | Cheng et al. |
| 5,557,024 A | 9/1996 | Cheng et al. |
| 5,827,491 A * | 10/1998 | Emerson ................. C01B 33/38 423/328.2 |
| 6,077,498 A | 6/2000 | Diaz Cabañas et al. |
| 6,756,030 B1 | 6/2004 | Rohde et al. |
| 6,936,744 B1 | 8/2005 | Cheng et al. |
| 6,984,764 B1 | 1/2006 | Roth et al. |
| 7,713,513 B2 | 5/2010 | Jan et al. |

FOREIGN PATENT DOCUMENTS

| | | |
|---|---|---|
| CN | 1500724 | 6/2004 |
| EP | 0 293 032 | 11/1988 |
| WO | WO 97/17290 | 5/1997 |
| WO | WO 2005/118476 | 12/2005 |
| WO | WO 2008/013644 | 1/2008 |

OTHER PUBLICATIONS

Baerlocher et al., "*Atlas of Zeolite Framework Types*", Elsevier, Fifth Revised Edition 2001.

\* cited by examiner

*Primary Examiner* — David M Brunsman
(74) *Attorney, Agent, or Firm* — Darryl M. Tyus

(57) ABSTRACT

The present invention provides an improved method for manufacturing high quality porous crystalline MCM-56 material. It also relates to the MCM-56 material manufactured by the improved method, catalyst compositions comprising same and use thereof in a process for catalytic conversion of hydrocarbon compounds. One such conversion process involves production of monoalkylated aromatic compounds, particularly ethylbenzene and cumene, by the liquid or partial liquid phase alkylation of alkylatable aromatic compound, particularly benzene.

15 Claims, No Drawings

MCM-56 MANUFACTURE

CROSS REFERENCE TO RELATED APPLICATIONS

This application is a 371 National Stage Application of International Application PCT/US2012/051181 filed Aug. 16, 2012, which claims the benefit of and priority to U.S. patent application Ser. No. 61/535,632 filed Sep. 16, 2011, the disclosures of which are incorporated herein by reference in their entireties.

FIELD OF THE INVENTION

The present invention relates to an improved method for manufacturing high quality porous crystalline MCM-56 material, the MCM-56 material manufactured by the improved method, catalyst compositions comprising the same and use thereof in a process for catalytic conversion of hydrocarbon compounds.

BACKGROUND OF THE INVENTION

Catalyst compositions comprising the porous crystalline MCM-56 material manufactured by this method may be used to effect various chemical conversions, and are especially valuable for use in a process for producing alkylaromatics, particularly ethylbenzene and cumene, or for use in a process for oligomerization of olefins, particularly for production of dimers, trimers and tetramers of olefins, e.g., ethylene, propylene, butylene, or mixtures thereof.

Ethylbenzene and cumene are valuable commodity chemicals that are used industrially for the production of styrene monomer and coproduction of phenol and acetone respectively. Ethylbenzene may be produced by a number of different chemical processes but one process that has achieved a significant degree of commercial success is the vapor phase alkylation of benzene with ethylene in the presence of a solid, acidic ZSM-5 zeolite catalyst. Examples of such ethylbenzene production processes are described in U.S. Pat. No. 3,751,504 (Keown), U.S. Pat. No. 4,547,605 (Kresge), and U.S. Pat. No. 4,016,218 (Haag).

More recently focus has been directed at liquid phase processes for producing ethylbenzene from benzene and ethylene since liquid phase processes operate at a lower temperature than their vapor phase counterparts and hence tend to result in lower yields of by-products. For example, U.S. Pat. No. 4,891,458 (Innes) describes the liquid phase synthesis of ethylbenzene with zeolite beta, whereas U.S. Pat. No. 5,334,795 (Chu) describes the use of MCM-22 in the liquid phase synthesis of ethylbenzene.

Cumene has for many years been produced commercially by the liquid phase alkylation of benzene with propylene over a Friedel-Craft catalyst, particularly solid phosphoric acid or aluminum chloride. More recently, however, zeolite-based catalyst systems have been found to be more active and selective for propylation of benzene to cumene. For example, U.S. Pat. No. 4,992,606 (Kushnerick) describes the use of MCM-22 in the liquid phase alkylation of benzene with propylene.

Alkylation processes for producing ethylbenzene and cumene in the presence of currently used catalysts inherently produce polyalkylated species as well as the desired mono-alkylated product. The polyalkylated species are typically transalkylated with benzene to produce additional mono-alkylated product, for example ethylbenzene or cumene, either by recycling the polyalkylated species to the alkylation reactor or, more frequently, by feeding the polyalkylated species to a separate transalkylation reactor having a transalkylation catalyst. Examples of catalysts which have been used in the alkylation of aromatic species, such as alkylation of benzene with ethylene or propylene, and in the transalkylation of polyalkylated species, such as polyethylbenzenes and polyisopropylbenzenes, are listed in U.S. Pat. No. 5,557,024 (Cheng) and include MCM-49, MCM-22, PSH-3, SSZ-25, zeolite X, zeolite Y, zeolite Beta, acid dealuminized mordenite and TEA-mordenite. Transalkylation over a small crystal (<0.5 micron) form of TEA-mordenite is also disclosed in U.S. Pat. No. 6,984,764.

MCM-56 is a layered oxide material, rather than a three dimensionally ordered zeolite, in which each layer in MCM-56 is porous and has a framework structure closely related to that of MCM-22 and other MCM-22 family materials.

The term "MCM-22 family material" (or "material of the MCM-22 family" or "molecular sieve of the MCM-22 family"), as used herein, includes one or more of:

(i) molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

(ii) molecular sieves made from a common second degree building block, being a 2-dimensional tiling of such MWW framework topology unit cells, forming a monolayer of one unit cell thickness, preferably one c-unit cell thickness;

(iii) molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and (iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize said molecular sieve are obtained by standard techniques using the K-alpha doublet of copper as the incident radiation and a diffractometer equipped with a scintillation counter and associated computer as the collection system. Materials that belong to the MCM-22 family include MCM-22 (described in U.S. Pat. No. 4,954,325); PSH-3 (described in U.S. Pat. No. 4,439,409); SSZ-25 (described in U.S. Pat. No. 4,826,667); ERB-1 (described in European Patent No. 0293032); ITQ-1 (described in U.S. Pat. No. 6,077,498); ITQ-2 (described in International Patent Publication No. WO97/17290); ITQ-30 (described in International Patent Publication No. WO2005118476); MCM-36 (described in U.S. Pat. No. 5,250,277); MCM-49 (described in U.S. Pat. No. 5,236,575); MCM-56 (described in U.S. Pat. No. 5,362,697); UZM-8 (described in U.S. Pat. No. 6,756,030); and UZM-8HS (described in U.S. Pat. No. 7,713,513). The entire contents of said patents are incorporated herein by reference.

It is to be appreciated the MCM-22 family molecular sieves described above are distinguished from conventional large pore zeolite alkylation catalysts, such as mordenite, in that the MCM-22 materials have 12-ring surface pockets which do not communicate with the 10-ring internal pore system of the molecular sieve.

The zeolitic materials designated by the IZA-SC as being of the MWW topology are multi-layered materials which have two pore systems arising from the presence of both 10 and 12 membered rings. The Atlas of Zeolite Framework Types classes five differently named materials as having this same topology: MCM-22, ERB-1, ITQ-1, ITQ-2, PSH-3, and SSZ-25.

The MCM-22 family molecular sieves have been found to be useful in a variety of hydrocarbon conversion processes. Examples of MCM-22 family molecular sieve are MCM-22, MCM-49, MCM-56, ITQ-1, ITQ-2, PSH-3, SSZ-25, ERB-1, UZM-8, and UZM-8HS.

MCM-56 and its synthesis are described in U.S. Pat. No. 5,362,697 (Fung) and U.S. Pat. No. 5,827,491 (Emerson). U.S. Pat. No. 5,453,554 (Cheng) discloses the use of MCM-56 as a catalyst in the alkylation of aromatic compounds with short chain (1 to 5 carbon atoms) alkylating agents. As disclosed in FIGS. 6 and 7 of U.S. Pat. No. 5,453,554, MCM-56 offers potential advantages over MCM-22 for the production of ethylbenzene and cumene, particularly under liquid phase conditions, since MCM-56 is a more active alkylation catalyst than its zeolitic counterpart MCM-22. The entire disclosures of U.S. Pat. Nos. 5,362,697, 5,827,491 and 5,453,554 are incorporated herein by reference.

When synthesizing MCM-56 by currently available means, impurity formation is a problem. Such preparation of MCM-56 presents a unique challenge, especially on a large scale, because it is an intermediate. The MCM-56 product produced may be transient and undergo further change during the manufacturing process. In particular, the initially exfoliated, randomly packed MCM-56 sheets (with MCM-22 topology and one 25 Å thick unit cell) become gradually organized into a 3-dimensional framework ordered in the c-direction, which is formally the zeolite MCM-49. This problem with the transient nature of MCM-56 is compounded by the difficulty in determining its complete formation and exhaustion of the amorphous synthesis gel.

According to the present invention, it has now unexpectedly been found that we can significantly avoid the above problems with a beneficial extension of the MCM-56 synthesis window. This improved method provides MCM-56 crystal product unencumbered by impurities, e.g., crystals of ferrierite, kenyaite, or MCM-22 family materials, such as MCM-49 materials, as identified by X-ray diffraction. This requires critical adjustment of the composition of the crystallization reaction mixture and control of the crystallization conditions, as detailed herein.

SUMMARY OF THE INVENTION

According to one aspect of the invention, there is provided an improved method for synthesizing in a commercially expedient manner a high quality porous crystalline MCM-56 material, which is identified by the X-ray diffraction pattern disclosed in U.S. Pat. Nos. 5,362,697 and 5,827,491, each patent incorporated herein by reference.

The improved method for synthesizing porous crystalline MCM-56 material comprises the steps of:
a) preparing a first reaction mixture containing sources of alkali or alkaline earth metal (M), e.g., sodium or potassium, cation, an oxide of a trivalent element X, e.g., aluminum, an oxide of a tetravalent element Y, e.g., silicon, preferably containing at least 30 wt. % of solid $YO_2$, zeolite seed crystals, preferably MCM-56 seed crystals, and water, said first reaction mixture having a composition, preferably, selected within the following ranges in terms of mole ratios of oxides:
$YO_2/X_2O_3$=5 to 35, e.g., 15 to 20;
$H_2O/YO_2$=10 to 70, e.g., 15 to 20;
$OH^-/YO_2$=0.05 to 0.20, e.g., 0.1 to 0.15;
$M/YO_2$=0.05 to 3.0, e.g., 0.11 to 0.15;
said first reaction mixture further comprising zeolite seed crystals in an amount from greater than or equal to 0.05 wt. %, or greater than or equal to 0.10 wt. %, or greater than or equal to 0.50 wt. %, or greater than or equal to 1.0 wt. %, to less than or equal to 5 wt. %, e.g., greater than or equal to 1 to less than or equal to 3 wt. %, based on the weight of the first reaction mixture;
b) adding directing agent R, e.g., hexamethyleneimine (HMI), to the reaction mixture of step a) to form a second reaction mixture having said directing agent R in terms of a mole ratio within the following range: $R/YO_2$=0.08 to 0.3, e.g., 0.1 to 0.2;
c) crystallizing the second reaction mixture of step b) under conditions of a temperature of from about 90° C. to about 175° C., preferably, from about 90° C. to less than 160° C., e.g., more preferably, from about 125° C. to about 175° C., a time for less than 90 hours, preferably, for less than 40 hours, e.g., more preferably, from about 20 to about 75 hours, preferably, at a stir rate of from about 40 to about 250 rpm, more preferably, from about 40 to about 100 rpm, to form a resulting mixture comprising crystals of said MCM-56 material; and
d) separating and recovering at least a portion of said crystals of said MCM-56 material from said resulting mixture of step c) to form as-synthesized MCM-56 material, wherein said crystals of as-synthesized MCM-56 material is characterized by the X-ray diffraction pattern shown in Table 1 below.

This improved method of manufacturing MCM-56 material produces a resulting mixture in step c) which comprises less than or equal to 10 wt. %, e.g., less than or equal to about 5 wt. %, less than or equal to about 1 wt. %, non-MCM-56 impurity crystals, based on the total weight of said MCM-56 crystals recovered from the second reaction mixture, as identified by X-ray diffraction. Such non-MCM-56 impurity crystals include, but are not limited to certain non-MCM-56 crystalline MCM-22 family materials, such as for example, MCM-49, UZM-8 and USM-8HS materials or mixtures thereof, as well as other materials, such as ferrierite, kenyaite or mixtures thereof.

The present invention also relates to the MCM-56 manufactured by the improved method and catalyst compositions comprising same. The invention also relates to hydrocarbon conversion processes using catalyst comprising the MCM-56 manufactured hereby. One such process involves production of monoalkylated aromatic compounds, particularly ethylbenzene and cumene, by the liquid or partial liquid phase alkylation of alkylatable aromatic compound, particularly benzene. Another such process involves production of oligomers from olefins.

DETAILED DESCRIPTION OF THE INVENTION

The high quality porous crystalline MCM-56 material made by the improved method for manufacturing of the present invention is characterized by the X-ray diffraction pattern as disclosed in U.S. Pat. Nos. 5,362,697 and 5,827,491, each patent incorporated herein by reference.

The X-ray diffraction pattern disclosed in U.S. Pat. Nos. 5,362,697 and 5,827,491 is shown below in Table 1 (as-synthesized) and Table 2 (as-calcined). In Tables 1 and 2, the intensities are defined relative to the d-spacing line at 12.4 Angstroms.

TABLE 1

| Interplanar d-Spacing (Angstroms) | Relative Intensity |
| --- | --- |
| 12.4 ± 0.2 | vs |
| 9.9 ± 0.3 | m |
| 6.9 ± 0.1 | w |
| 6.4 ± 0.3 | w |
| 6.2 ± 0.1 | w |
| 3.57 ± 0.07 | m-s |
| 3.44 ± 0.07 | vs |

TABLE 2

| Interplanar d-Spacing (Angstroms) | Relative Intensity |
| --- | --- |
| 12.4 ± 0.2 | vs |
| 9.9 ± 0.3 | m |
| 6.9 ± 0.1 | w |
| 6.2 ± 0.1 | s |
| 3.55 ± 0.07 | m-s |
| 3.42 ± 0.07 | vs |

The above X-ray diffraction data were collected with a Scintag diffraction system, equipped with a germanium solid state detector, using copper K-alpha radiation. The is diffraction data were recorded by step-scanning at 0.02 degrees of two-theta, where theta is the Bragg angle, and a counting time of 10 seconds for each step. The interplanar spacings, d-spacings, were calculated in Angstrom units (A), and the relative intensities of the lines, $I/I_o$ is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (60-100), s=strong (40-60), m=medium (20-40) and w=weak (0-20). It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, and thermal and/or hydrothermal history.

The method for producing the porous crystalline MCM-56 comprises the steps of:

a) preparing a first reaction mixture containing sources of alkali or alkaline earth metal (M), e.g., sodium or potassium, cation, an oxide of a trivalent element X, e.g., aluminum, an oxide of a tetravalent element Y, e.g., silicon, preferably, containing at least 30 wt. % of solid $YO_2$, zeolite seed crystals, preferably, MCM-56 seed crystals, and water, said first reaction mixture having a composition in terms of mole ratios of oxides, preferably, selected within the following ranges:

$YO_2/X_2O_3$=5 to 35, e.g., 15 to 20;
$H_2O/YO_2$=10 to 70, e.g., 15 to 20;
$OH^-/YO_2$=0.05 to 0.20, e.g., 0.1 to 0.15;
$M/YO_2$=0.05 to 3.0, e.g., 0.11 to 0.15;

said first reaction mixture further comprising zeolite seed crystals in an amount from greater than or equal to 0.05 wt. %, or greater than or equal to 0.10 wt. %, or greater than or equal to 0.50 wt. %, or greater than or equal to 1.0 wt. %, to less than or equal to 5 wt. %, e.g., greater than or equal to 1 to less than or equal to 3 wt. %, based on the weight of the first reaction mixture;

b) adding directing agent R, e.g., preferably, hexamethyleneimine (HMI), to the reaction mixture of step a) to form a second reaction mixture having said directing agent R in terms of a mole ratio within the following range: $R/YO_2$=0.08 to 0.3, e.g., 0.1 to 0.2;

c) crystallizing the second reaction mixture of step b) under conditions of a temperature of from about 90° C. to about 175° C., preferably, from about 90° C. to less than 160° C., e.g., from about 125° C. to about 175° C., and a time for less than 90 hours, preferably, for less than 40 hours, e.g., from about 20 to about 75 hours, at a stir rate of from about 40 to about 250 rpm, preferably, from about 40 to about 100 rpm, to form a resulting mixture comprising crystals of said MCM-56 material and less than or equal to 10 wt. %, e.g., less than or equal to about 5 wt. %, of non-MCM-56 impurity crystals, based on the total weight of said MCM-56 crystals in said second reaction mixture, as identified by X-ray diffraction, such as, for example, crystalline MCM-22 family materials (defined below), such as MCM-49 material, or ferrierite, kenyaite or mixtures thereof; and d) separating and recovering at least a portion of crystals of said MCM-56 material from the resulting mixture of step c) to form as-synthesized MCM-56 material wherein said crystals of as-synthesized MCM-56 material is characterized by the X-ray diffraction pattern shown in Table 1 above.

The second reaction mixture of step b) has a solids content of range from at least 12 wt. %, or at least 15 wt. %, or at least 18 wt. %, or at least 20 wt. %, or at least 30 wt. % up to less than 40 wt. %, or less than 50 wt. %, or less than 60 wt. %., based on the weight of the second reaction mixture. Preferably, the solids content of the second reaction mixture of step b) is less than 30 wt. %, based on the weight of the second reaction mixture.

In order to achieve the required first reaction mixture composition for this improved method, some selective critical changes have to be made to the method for making MCM-56 material as compared to the current practice. For example, the addition of caustic NaOH is eliminated, except as a component of, for example, sodium aluminate. Also, the organic directing agent is not added to the first reaction mixture during its formation, but a controlled amount of organic directing agent reduced to nearly stoichiometric amounts is only added to the fully formed first reaction mixture to form the second reaction mixture. Further, zeolite seeds crystals, preferably, zeolite seed crystals of MCM-22 family material, more preferably, zeolite seed crystals of MCM-56, are added to the first reaction mixture based on its total weight such that the amount of seed crystals is from greater than or equal to 0.05 wt. %, or greater than or equal to 0.10 wt. %, or greater than or equal to 0.50 wt. %, or greater than or equal to 1.0 wt. %, to less than or equal to 5 wt. %, e.g., from greater than or equal to 1 to less than or equal to 3 wt. %, of the first reaction mixture. Surprisingly, adding MCM-56 seed crystals to the first reaction mixture required for this improved method does not accelerate the formation of impurities as would normally be expected in such a crystallization procedure.

The improved method of this invention beneficially stabilizes and extends the crystallization window in step c) of the method to avoid impurity, e.g., MCM-49 material, formation; reduces organic loading in the crystallization step c) lowering cost, especially important in commercial MCM-56 manufacturing; and accelerates the crystallization rate in step c) to greatly improve throughput. Further, the intentional addition of the preferred MCM-56 seed crystals swamps out normally expected effects of acceleration of crystallization of impurities caused by residual particles in the crystallizer. This is especially important in commercial manufacturing. In the improved method, seeding did not accelerate the introduction of impurities.

In the present improved method, the source of $YO_2$ must be comprise solid $YO_2$, for example at least about 30 wt. % solid $YO_2$. When $YO_2$ is silica, the use of a silica source containing at least about 30 wt. % solid silica, e.g., Ultrasil, now known as Sipernat (a precipitated, spray dried silica containing about 90 wt. % silica) or HiSil (a precipitated hydrated silica containing about 87 wt. % silica, about 6 wt. % free $H_2O$ and about 4.5 wt. % bound $H_2O$ of hydration and having a particle size of about 0.02 micron) favors crystalline MCM-56 formation from the above second reaction mixture under the synthesis conditions required. Preferably, therefore, the $YO_2$, e.g., silica, source contains at least about 30 wt. % solid $YO_2$, e.g., silica, and more preferably at least about 40 wt. % solid $YO_2$, e.g., silica.

Organic directing agent R may be selected from the group consisting of cycloalkylamine, azacycloalkane, diazacycloalkane, and combinations thereof, alkyl comprising from 5 to 8 carbon atoms. Non-limiting examples of R include cyclopentylamine, cyclohexylamine, cycloheptylamine, hexamethyleneimine (HMI), heptamethyleneimine, homopiperazine, and combinations thereof.

It is noted that the reaction mixture components can be supplied by more than one source. The reaction mixture can be prepared either batchwise or continuously.

Step c) crystallization of the second reaction mixture in the present method is preferably carried out under stirred conditions in a suitable reactor vessel, such as for example, polypropylene containers or Teflon lined or stainless steel autoclaves. However, it is within the scope of this invention for crystallization to occur under static conditions.

The useful ranges of conditions for crystallization in this method are a temperature from about 90° C. to about 175° C., preferably, from about 90° C. to less than 160° C., e.g., from about 125° C. to about 175° C., and a time for less than 90 hours, preferably, for less than 40 hours, e.g., from about 20 to about 75 hours, preferably, at a stir rate of from about 40 to about 250 rpm, more preferably, from about 40 to about 100 rpm, to form a resulting mixture comprising high quality crystals of MCM-56 material and less than or equal to 10 wt. % non-MCM-56 impurity crystals, based on the total weight of said MCM-56 crystals recovered from the reaction mixture, as identified by X-ray diffraction. Thereafter, the crystals of as-synthesized MCM-56 material are separated from the resulting liquid mixture and recovered in step d).

Another embodiment of the present improved method comprises aging the second reaction mixture of step b) prior to crystallizing step c) for from about 0.5 to about 48 hours, for example from about 0.5 to about 24 hours, at a temperature of from about 25 to about 75° C. Preferably, the second reaction mixture was agitated with stirring at, for example 50 rpm, for less than 48 hours at ambient temperature.

Catalyst comprising the MCM-56 material manufactured hereby may be used to effect conversion in chemical reactions, and is particularly useful in a process for selectively producing a desired monoalkylated aromatic compound comprising the step of contacting an alkylatable aromatic compound with an alkylating agent in the presence of the catalyst under at least partial liquid phase conditions. Another aspect of the present invention, therefore, is an improved alkylation catalyst comprising the high quality MCM-56 manufactured by the present improved method for use in a process for the selective production of monoalkyl benzene comprising the step of reacting benzene with an alkylating agent under alkylation conditions in the presence of said alkylation catalyst. Using the present catalyst to effect alkylation of an alkylatable aromatic compound, the alkylating agent may include an alkylating aliphatic group having 1 to 5 carbon atoms. The alkylating agent may be, for example, ethylene or propylene and the alkylatable aromatic compound in such an instance may suitably be benzene.

The MCM-56 manufactured hereby may be used as a catalyst component to effect hydrocarbon compound conversion, and is particularly useful as catalyst in a process for selectively producing a desired monoalkylated aromatic compound comprising the step of contacting an alkylatable aromatic compound with an alkylating agent under at least partial liquid phase conditions. For example, alkylation catalyst comprising the high quality MCM-56 manufactured by the present improved method may be used in a process for the selective production of monoalkylated benzene comprising the step of reacting benzene with an alkylating agent such as, for example, ethylene or propylene, under alkylation conditions in the presence of said alkylation catalyst.

The term "aromatic" in reference to the alkylatable aromatic compounds which may be useful as feedstock in a process beneficially utilizing the present catalyst is to be understood in accordance with its art-recognized scope. This includes alkyl substituted and unsubstituted mono- and polynuclear compounds. Compounds of an aromatic character that possess a heteroatom are also useful provided they do not act as catalyst poisons under the reaction conditions selected.

Substituted aromatic compounds that can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups that do not interfere with the alkylation reaction.

Suitable aromatic compounds include benzene, naphthalene, anthracene, naphthacene, perylene, coronene, and phenanthrene, with benzene being preferred.

Generally, the alkyl groups that can be present as substituents on the aromatic compound contain from 1 to about 22 carbon atoms and usually from about 1 to 8 carbon atoms, and most usually from about 1 to 4 carbon atoms.

Suitable alkyl substituted aromatic compounds include toluene, xylene, isopropylbenzene, n-propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic compounds can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecyltoluene, etc. Very often alkylate is obtained as a high boiling fraction in which the alkyl group attached to the aromatic nucleus varies in size from about $C_6$ to about $C_{12}$. When cumene or ethylbenzene is the desired product, the present process produces acceptably little by-products such as xylenes. The xylenes made in such instances may be less than about 500 ppm.

Reformate containing a mixture of benzene, toluene and/or xylene constitutes a useful feed for the alkylation process of this invention.

The alkylating agents which are useful as feedstock in a process beneficially utilizing the catalyst of this invention generally include any aliphatic or aromatic organic compound having one or more available alkylating aliphatic groups capable of reaction with the alkylatable aromatic compound, preferably with the alkylating group possessing from 1 to 5 carbon atoms. Examples of suitable alkylating agents are olefins such as ethylene, propylene, the butenes, and the pentenes; alcohols (inclusive of monoalcohols, dialcohols, trialcohols, etc.) such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth.

Mixtures of light olefins are useful as alkylating agents in the alkylation process utilizing the catalyst of this invention. Also, such mixtures of light olefins are useful as reactants in the oligomerization process utilizing the catalyst of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents and oligomerization reactants herein. For example, a typical FCC light olefin stream possesses the following composition in Table 3:

TABLE 3

|  | Wt. % | Mole % |
|---|---|---|
| Ethane | 3.3 | 5.1 |
| Ethylene | 0.7 | 1.2 |
| Propane | 4.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

For these uses of catalyst comprising the MCM-56 manufactured by the present method, products may include ethylbenzene from the reaction of benzene with ethylene, cumene from the reaction of benzene with propylene, ethyltoluene from the reaction of toluene with ethylene, cymenes from the reaction of toluene with propylene, and sec-butylbenzene from the reaction of benzene and n-butenes, a mixture of heavier olefins from the oligomerization of light olefins. Particularly preferred uses of this catalyst relate to the production of cumene by the alkylation of benzene with propylene, production of ethylbenzene by the alkylation of benzene with ethylene, and oligomerization of ethylene, propylene, butylene, or mixtures thereof.

The hydrocarbon compound conversion processes contemplated for use of this catalyst include, but are not limited to, oligomerization of olefins and may be conducted such that the reactants are brought into contact with the required catalyst in a suitable reaction zone such as, for example, in a flow reactor containing a fixed bed of the catalyst composition, under effective conversion conditions. Such conditions include a temperature of from about 0 to about 1000° C., preferably from about 0 to about 800° C., a pressure of from about 0.1 to about 1000 atmospheres, preferably from about 0.125 to about 500 atmospheres, and a feed weight hourly space velocity (WHSV) of from about 0.01 to 500 $hr^{-1}$, preferably from about 0.1 to about 100 $hr^{-1}$. If a batch reactor is used, the reaction time will be from about 1 minute to about 100 hours, preferably from about 1 hour to about 10 hours.

An alkylation process utilizing this catalyst may be conducted such that the reactants, i.e., the alkylatable aromatic compound and the alkylating agent, are brought into contact with the catalyst in a suitable reaction zone such as, for example, a flow reactor containing a fixed bed of the catalyst composition, under effective alkylation conditions. Such conditions include a temperature of from about 0 to about 500° C., preferably from about 10 to about 260° C., a pressure of from about 0.2 to about 250 atmospheres, preferably from about 1 to about 55 atmospheres, a molar ratio of alkylatable aromatic compound to alkylating agent of from about 0.1:1 to about 50:1, preferably from about 0.5:1 to about 10:1, and a feed weight hourly space velocity (WHSV) based on the alkylating agent of from about 0.1 to 500 $hr^{-1}$, preferably from about 0.5 to about 100 $hr^{-1}$.

The reactants can be in either the vapor phase or partially or completely in the liquid phase and can be neat, i.e., free from intentional admixture or dilution with other material, or they can be brought into contact with the alkylation catalyst composition with the aid of carrier gases or diluents such as, for example, hydrogen or nitrogen.

When benzene is alkylated with ethylene to produce ethylbenzene, the alkylation reaction is preferably carried out in the liquid phase under conditions including a temperature of from about 150 to about 300° C., more preferably from about 170 to about 260° C.; a pressure up to about 204 atmospheres, more preferably from about 20 atmospheres to about 55 atmospheres; a weight hourly space velocity (WHSV) based on the ethylene alkylating agent of from about 0.1 to about 20 $hr^{-1}$, more preferably from about 0.5 to about 6 $hr^{-1}$; and a ratio of benzene to ethylene in the alkylation reactor of from about 0.5:1 to about 100:1 molar, preferably from about 0.5:1 to about 30:1 molar, more preferably from about 1:1 to about 10:1 molar.

When benzene is alkylated with propylene to produce cumene, the reaction may also take place under liquid phase conditions including a temperature of up to about 250° C., preferably up to about 150° C., e.g., from about 10 to about 125° C.; a pressure of about 250 atmospheres or less, e.g., from about 1 to about 30 atmospheres; a weight hourly space velocity (WHSV) based on propylene alkylating agent of from about 0.1 $hr^{-1}$ to about 250 $hr^{-1}$, preferably from about 1 $hr^{-1}$ to about 50 $hr^{-1}$; and a ratio of benzene to propylene in the alkylation reactor of from about 0.5:1 to about 100:1 molar, preferably from about 0.5:1 to about 30:1 molar, more preferably from about 1:1 to about 10:1 molar.

The catalyst of the present invention may be used in a variety of forms. For certain applications of the catalyst, the average particle size of the crystalline molecular sieve component may be from about 0.05 to about 200 microns, for example, from 20 to 200 microns.

When used as catalyst for alkylation, the alkylation reactor effluent contains the excess aromatic feed, monoalkylated product, polyalkylated products, and various impurities. The aromatic feed is recovered by distillation and recycled to the alkylation reactor. Usually a small bleed is taken from the recycle stream to eliminate unreactive impurities from the loop. The bottoms from the distillation may be further distilled to separate monoalkylated product from polyalkylated products and other heavies.

The polyalkylated products separated from the alkylation reactor effluent may be reacted with additional aromatic feed in a transalkylation reactor, separate from the alkylation reactor, over a suitable transalkylation catalyst. The transalkylation catalyst may comprise one or a mixture of crystalline molecular sieves having the structure of zeolite Beta, zeolite Y (natural or synthetic forms), mordenite (natural and synthetic forms) or an MCM-22 family having an X-ray diffraction pattern including d-spacing maxima at 12.4±0.25, 6.9±0.15, 3.57±0.07 and 3.42±0.07 Angstroms.

The X-ray diffraction data used to characterize said above molecular sieve structures as well as in the Examples below are obtained by standard techniques using the K-alpha doublet of copper as the incident radiation and a diffractometer equipped with a scintillation counter and associated computer as the collection system. This is disclosed in U.S. Pat. Nos. 5,362,697 and 5,827,491, each incorporated herein by reference.

Zeolite Beta is disclosed in U.S. Pat. No. 3,308,069. Zeolite Y and mordenite occur naturally but may also be used in one of their synthetic forms, such as Ultrastable Y (USY), which is disclosed in U.S. Pat. No. 3,449,070, Rare-earth exchanged Y (REY), which is disclosed in U.S. Pat. No. 4,415,438, and TEA-mordenite (i.e., synthetic mordenite prepared from a reaction mixture comprising a tetraethylammonium directing agent), which is disclosed in U.S. Pat. Nos. 3,766,093 and 3,894,104. However, in the case of TEA-mordenite for use in the transalkylation catalyst, the particular synthesis regimes described in the patents noted lead to the production of a mordenite product composed of predominantly large crystals with a size greater than 1 micron and typically around 5 to 10 micron. It has been found that controlling the synthesis so that the resultant TEA-mordenite has an average crystal size of less than 0.5 micron results in a transalkylation catalyst with materially enhanced activity for liquid phase aromatics transalkylation.

The catalyst of the present invention may include an inorganic oxide material matrix or binder. Such matrix materials include synthetic or naturally occurring substances as well as inorganic materials such as clay, silica and/or metal oxides, e.g., alumina The latter may be either naturally occurring or in the form of gelatinous precipitates or gels including mixtures of silica and metal oxides. Naturally occurring clays which can be composited with the inorganic oxide material include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

Specific useful catalyst matrix or binder materials employed herein include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

The relative proportions of crystalline molecular sieve and binder or matrix, if present, may vary widely with the crystalline molecular sieve content ranging from about 1 to about 99 percent by weight, and more usually in the range of about 30 to about 80 percent by weight of the total catalyst. Of course, the catalyst may comprise a self-bound molecular sieve or an unbound molecular sieve, thereby being about 100% crystalline molecular sieve MCM-56.

The catalyst of the present invention, or its crystalline molecular sieve component, may or may not contain added functionalization, such as, for example, a metal of Group VI (e.g., Cr and Mo), Group VII (e.g., Mn and Re) or Group VIII (e.g., Co, Ni, Pd and Pt), or phosphorus.

The surface area of a molecular sieve may be measured by the Brunauer-Emmett-Teller (BET) test method using adsorption-desorption of nitrogen (temperature of liquid nitrogen, 77 K). The internal surface area may be calculated using t-plot of the Brunauer-Emmett-Teller (BET) measurement. The external surface area is calculated by subtracting the internal surface area from the overall surface area measured by the Brunauer-Emmett-Teller (BET) measurement.

Non-limiting examples of the invention are described with reference to the following experiments. In these experiments, the BET test method was used for surface area measurement described in ASTM D3663-03. The crystallization time was to complete crystallization or a point when crystallization appeared to be complete or extremely slow. Catalyst activity was measured in part by the standard Alpha Activity test. Unless otherwise specified, the reference to "parts" is a reference to "parts by weight."

EXAMPLES

Example 1

Sixteen parts water and 1 part 45% sodium aluminate solution (22% $Al_2O_3$, 19.5% $Na_2O$), were charged to an autoclave reactor. The solution was agitated at 60 rpm for 1 to 24 hours at ambient temperature. Then 3.14 parts $SiO_2$ (Ultrasil-VN3PM-Modified, now known as Sipernat 320C and obtainable from Evoniks, formerly Degussa) and 0.02 part MCM-56 seeds (drycake) were added to form the first reaction mixture. The reactor was sealed and pressure tested. Then 0.53 part hexamethyleneimine (HMI as 100% organic) was charged to the reactor to form the second reaction mixture. The second reaction mixture was agitated at 50 rpm for less than 48 hours at ambient temperature. The reactor was then heated to 151° C. at 50 rpm and the contents were allowed to crystallize for 28 hours forming a resulting mixture. The resulting mixture comprised MCM-56 and less than 10 wt. % impurity as confirmed by X-ray diffraction. The reactor was cooled to 127° C. and the organic removed via the HMI/water azeotrope, i.e., "flashed", into a collection vessel. The flashed solvent ("condensate") was collected for recycle by combining with additional fresh HMI for subsequent batches. The reactor was cooled and the product discharged. The extent of crystallization was confirmed by BET surface area. Formulation particulars and results for this Example 1 are reported in Tables 4 and 5 below.

Example 1.1

Sixteen parts water, 1 part 45% sodium aluminate solution (22% $Al_2O_3$, 19.5% $Na_2O$), 3.13 parts $SiO_2$ (Ultrasil-VN3PM-Modified), 0.02 part MCM-56 seeds, and 0.53 part hexamethyleneimine (HMI as 100% organic) were charged to an autoclave reactor. The reactor was sealed and pressure tested. The resulting solution was agitated at 250 rpm for less than 48 hours at ambient temperature. The autoclave was then heated to 151° C. at 250 rpm and the contents were allowed to react for 72 hours. At that time it was confirmed by X-ray diffraction that the product was amorphous. The reactor was cooled to 127° C. and the organic removed via the HMI/water azeotrope, i.e., "flashed", into a collection vessel. The reactor was cooled and the product discharged. The lack of crystallization was confirmed by BET surface area. Formulation particulars and results for this Example 1.1 are reported in Tables 4 and 5 below.

Example 1.2

Sixteen parts water, 1 part 45% sodium aluminate solution (22% $Al_2O_3$, 19.5% $Na_2O$), 3.14 parts $SiO_2$ (Ultrasil-VN3PM-Modified) and 0.02 part MCM-56 seeds (drycake) were charged to an autoclave reactor to form the first reaction mixture, and then 0.53 part hexamethyleneimine (HMI as 100% organic) was charged to the reactor to form the second reaction mixture. The reactor was sealed and pressure tested. The second reaction mixture was agitated at 250 rpm for less than 48 hours at ambient temperature. The reactor was heated to 151° C. at 250 rpm and the contents were allowed to crystallize for 72 hours forming a resulting mixture. The resulting mixture comprised MCM-56 and less than 10 wt. % impurity as confirmed by X-ray diffraction. The reactor was cooled to 127° C. and the organic removed via the HMI/water azeotrope, i.e., "flashed", into a collection vessel. The reactor was cooled and the product discharged. For some crystals, the extent of crystallization was confirmed by BET surface area. Formulation particulars and results for this Example 1.2 are reported in Tables 4 and 5 below.

Example 2

Sixteen parts water and 1 part 45% sodium aluminate solution (22% $Al_2O_3$, 19.5% $Na_2O$), were charged to an autoclave reactor. The solution was agitated at 60 rpm for 1 to 24 hours at ambient temperature. Then 3.14 parts $SiO_2$ (Ultrasil-VN3PM-Modified) and 0.02 part MCM-56 seeds (drycake) were added to form the first reaction mixture. The reactor was sealed and pressure tested. Then 0.53 part hexamethyleneimine (HMI as 100% organic) was charged to the reactor to form the second reaction mixture. The second reaction mixture was agitated at 50 rpm for less than 48 hours at ambient temperature. The reactor was sealed, heated to 141.5° C. at 50 rpm and the contents were allowed to crystallize for 36 hours forming a resulting mixture. The resulting mixture comprised MCM-56 and less than 10 wt. % impurity as confirmed by X-ray diffraction. The reactor was cooled to 127° C. and the organic removed via the HMI/water azeotrope, i.e., "flashed", into a collection vessel. The flashed solvent ("condensate") was collected for recycle by combining with additional fresh HMI for subsequent batches. The reactor was cooled and the product discharged. The extent of crystallization was confirmed by BET surface area. Formulation particulars and results for this Example 2 are reported in Tables 4 and 5 below.

Example 3

To approximately 0.02 part MCM-56 seeds in the as-synthesized condition, left in the reactor from a previous MCM-56 crystallization, was added 0.72 part water and 1 part 5% USALCO, a sodium aluminate solution (as-received solution diluted with additional water from the original 22% $Al_2O_3$ and 19.5% $Na_2O$ to be 2.9% $Al_2O_3$ and 1.8% $Na_2O$) in an autoclave reactor. The solution was agitated at 60 rpm for 1 to 24 hours at ambient temperature. Then 0.31 part $SiO_2$ (Ultrasil-VN3PM-Modified) was added to form the first reaction mixture. The reactor was sealed and pressure tested. Then 0.053 part hexamethyleneimine (HMI as 100% organic) was charged to the reactor to form the second reaction mixture. The second reaction mixture was agitated at 60 rpm for less than 48 hours at ambient temperature. The reactor was sealed, heated to 148.5° C. at 60 rpm and the contents were allowed to crystallize for 36 hours forming a resulting mixture. The resulting mixture comprised MCM-56 and less than 10 wt. % impurity as confirmed by X-ray diffraction. The reactor was cooled to 127° C. and the organic removed via the HMI/water azeotrope, i.e., "flashed", into a collection vessel. The flashed solvent ("condensate") was collected for recycle by combining with additional fresh HMI for subsequent batches. The reactor was cooled and the product discharged. The extent of crystallization was confirmed by BET surface area. Formulation particulars and results for this Example 3 are reported in Tables 4 and 5 below.

Example 3.1

To 0.702 parts water was added 1 part 5% sodium aluminate obtainable from USALCO (as-received solution diluted with additional water from the original 22% $Al_2O_3$ and 19.5% $Na_2O$ to be 2.9% $Al_2O_3$ and 1.8% $Na_2O$) in an autoclave reactor. The solution was agitated at 60 rpm for 1 to 24 hours at ambient temperature. Then 0.31 part $SiO_2$ (Ultrasil-VN3PM-Modified) was added to form a first reaction mixture, but without seed crystals. The reactor was sealed and pressure tested. Then 0.053 part hexamethyleneimine (HMI as 100% organic) was charged to the reactor to form the second reaction mixture. The second reaction mixture was agitated at 60 rpm for less than 48 hours at ambient temperature. The reactor was sealed, heated to 148.5° C. at 60 rpm and the contents were allowed to crystallize for 61 hours. MCM-56 was confirmed by X-ray diffraction. The reactor was cooled to 127° C. and the organic removed via the HMI/water azeotrope, i.e., "flashed", into a collection vessel. The flashed solvent ("condensate") was collected for recycle by combining with additional fresh HMI for subsequent batches. The reactor was cooled and the product discharged. The extent of crystallization was confirmed by BET surface area. Formulation particulars and results for this Example 3.1 are reported in Tables 4 and 5 below.

Example 4

To approximately 0.02 part MCM-56 seeds in the as-synthesized condition, left in the reactor from previous MCM-56 crystallization, was added 0.72 part water and 1 part 5% USALCO (as-received solution diluted with additional water from the original 22% $Al_2O_3$ and 19.5% $Na_2O$ to be 2.9% $Al_2O_3$ and 1.8% $Na_2O$) in an autoclave reactor. The solution was agitated at 60 rpm for 1 to 24 hours at ambient temperature. Then 0.32 part $SiO_2$ (Ultrasil-VN3PM-Modified) was added to form the first reaction mixture. The reactor was sealed and pressure tested. Then 0.17 part hexamethyleneimine (HMI as 100% organic) was charged to the reactor to form the second reaction mixture. The second reaction mixture was agitated at 60 rpm for less than 48 hours at ambient temperature. The reactor was sealed, heated to 141.5° C. at 60 rpm and the contents were allowed to crystallize for 33 hours, at which time crystallization was stopped due to the resulting mixture not progressing to full crystallization. The reactor was cooled to 127° C. and the organic removed via the HMI/water azeotrope, i.e., "flashed", into a collection vessel. The reactor was cooled and the product discharged. The lack of crystallization was confirmed by BET surface area. Formulation particulars and results for this Example 4 are reported in Tables 4 and 5 below.

Example 4.1

One part 5% USALCO (as-received solution diluted with additional water from the original 22% $Al_2O_3$ and 19.5% $Na_2O$ to be 2.9% $Al_2O_3$ and 1.8% $Na_2O$) and 0.72 part water were charged to an autoclave reactor. Then 0.32 part $SiO_2$ (Ultrasil-VN3PM-Modified) was added. The reactor was sealed and pressure tested. The solution was agitated at 60 rpm for 1 to 24 hours at ambient temperature. Then 0.17 part hexamethyleneimine (HMI as 100% organic) was charged to the reactor to form the second reaction mixture. The second reaction mixture was agitated at 60 rpm for less than 48 hours at ambient temperature. The reactor was sealed, heated to 141.5° C. at 60 rpm and the contents were allowed to crystallize for 69 hours. At that time crystallization to MCM-56 was confirmed by X-ray diffraction, the reactor was cooled to 127° C. and the organic removed via the HMI/water azeotrope, i.e., "flashed", into a collection vessel. The reactor was cooled and the product discharged. The extent of crystallization was confirmed by BET surface area. Formulation particulars and results for this Example 4.1 are reported in Tables 4 and 5 below.

Example 5

Sixteen parts water and 1 part 45% sodium aluminate solution (22% $Al_2O_3$, 19.5% $Na_2O$), were charged to an autoclave reactor. The solution was agitated between 60 and 250 rpm for 1 to 24 hours at ambient temperature. Then 3.43 parts $SiO_2$ (Ultrasil-VN3PM) was added to the reactor. The reactor was sealed and pressure tested. Then 0.53 parts hexamethyleneimine (HMI as 100% organic) were charged to the reactor to form the second reaction mixture. The second reaction mixture was agitated at 60 rpm for less than 48 hours at ambient temperature. The reactor was sealed, heated to 148.5° C. at 60 rpm and the contents were allowed to crystallize for 56 hours. At that time crystallization to MCM-56 was confirmed by X-ray diffraction, the reactor was cooled to 127° C. and the organic removed via the HMI/water azeotrope, i.e., "flashed", into a collection vessel. The reactor was cooled and the product discharged. The extent of crystallization was confirmed by BET surface area. Formulation particulars and results for this Example 5 are reported in Tables 4 and 5 below.

TABLE 4

| Example | $SiO_2/Al_2O_3$ | OH/$SiO_2$ | $H_2O$/$SiO_2$ | R/$SiO_2$ | M/$SiO_2$ | Seeds* |
|---|---|---|---|---|---|---|
| 1 | 19 | 0.12 | 19 | 0.11 | 0.14 | 1.0 |
| 1.1 | 19 | 0.12 | 19 | 0.11 | 0.14 | 0.0 |
| 1.2 | 19 | 0.12 | 19 | 0.11 | 0.14 | 1.0 |
| 2 | 19 | 0.12 | 19 | 0.11 | 0.14 | 1.0 |
| 3 | 17 | 0.11 | 18 | 0.11 | 0.13 | 1.0 |
| 3.1 | 17 | 0.11 | 18 | 0.11 | 0.13 | 0.0 |
| 4 | 17 | 0.11 | 19 | 0.34 | 0.12 | 1.0 |
| 4.1 | 17 | 0.11 | 19 | 0.36 | 0.12 | 0.0 |
| 5 | 21 | 0.11 | 17 | 0.10 | 0.13 | 0.0 |

*Seeds in weight percent based on the weight of the crystals recovered from the reaction mixture.

TABLE 5

| Example | Temperature, ° C. | Stir Rate, rpm | Time** |
|---|---|---|---|
| 1 | 151 | 50 | 28 |
| 1.1 | 151 | 250 | 72 (amorphous) |
| 1.2 | 151 | 250 | 72 |
| 2 | 141.5 | 50 | 36 |
| 3 | 148.5 | 60 | 36 |
| 3.1 | 148.5 | 60 | 61 |
| 4 | 141.5 | 60 | 33 (not fully crystallized) |
| 4.1 | 141.5 | 60 | 69 (very slow) |
| 5 | 148.5 | 60 | 56 |

**Time in hours until crystallization is complete or not progressing.

It is observed from Example 1.1 that the first reaction mixture without the required MCM-56 seed crystals to form a second reaction mixture, even at higher sheer and the same temperature, did not crystallize in over 2.5 times the crystallization time for Example 1. Example 1.2 shows that repeating Example 1.1 except with a first reaction mixture comprising the seeds provides crystalline MCM-56. Example 3 shows that order of seed addition for the first reaction mixture does not adversely affect the outcome, and that the MCM-56 seeds may be as-synthesized. Example 3.1 compared to Example 3 demonstrates that crystallization is significantly slower without forming the first reaction mixture required of the present method. Example 4.1 compared to Example 4 demonstrates that crystallization is significantly slower without forming the first or second reaction mixture required of the present method.

Example 6

To formulate catalyst comprising MCM-56 manufactured by the present improved process, 60 parts MCM-56 product recovered from Example 1 (100% solids basis) was combined with 40 parts UOP Versal 300™ pseudoboehmite alumina (100% solids basis). The combined dry powder was placed in a lab scale Lancaster Muller and mixed for 30 minutes. Sufficient water was added during the mixing to produce an extrudable paste. The extrudable paste was formed into 1/20" quadrulobe extrudate using a 2 inch laboratory Bonnot extruder. The extrudate was dried overnight at 121° C. in an oven. The dried extrudate was heated at a rate of 2.4° C. per minute to 538° C. and held for 3 hours under flowing nitrogen. The extrudate was then cooled to ambient temperature and humidified with saturated air overnight. The humidified extrudate was exchanged with 5 milliliters of 1 N ammonium nitrate per gram of catalyst for 1 hour. The ammonium nitrate exchange was repeated with fresh ammonium nitrate. The ammonium exchanged extrudate was then washed with 5 volumes deionized water per volume of extrudate to remove residual nitrate. The washed extrudate was dried overnight in an oven at 121° C. The extrudate was then calcined in a nitrogen/air mixture at the following conditions. The extrudate was ramped from ambient temperature to 426° C. in a 1% $O_2$/99% $N_2$ mixture at a heating rate of 28° C. per hour and held at 426° C. for 3 hours. The temperature was then increased to 482° C. at a rate of 28° C. per hour and held at 482° C. for an additional 3 hours. At 482° C. the $O_2$ was increased in stages to 7.6% $O_2$. The extrudate was held at 482° C. in the 7.6% $O_2$/92.4% head pressure was maintained on the autoclave using a nitrogen blanket. Liquid product samples were taken at 30, 60, 90, 120 and 180 minutes. The liquid samples were analyzed on an Agilent 5890 GC. The GC data was fitted to a $2^{nd}$ order kinetic model. The $2^{nd}$ order kinetic rate constant for the conversion of benzene and propylene was calculated along with the ratio of diisopropylbenzene (DiPB) to cumene and triisopropylbenzene (TriPB) to cumene at 3 hours time-on-stream. This was repeated for each catalyst.

Table 6 summarizes the physical and catalytic properties of the catalyst compositions of above Examples 6, 7, 8 and 9.

TABLE 6

|  | Example 6 | | | Example 7 | Example 8 | Example 9 |
| --- | --- | --- | --- | --- | --- | --- |
| MCM-56/$Al_2O_3$, wt. % | 40/60 | 40/60 | 40/60 | 60/40 | 80/20 | 20/80 |
| Na, wt. % | 0.0269 | 0.0170 | 0.0215 | 0.0435 | 0.0376 | 0.0074 |
| Alpha Activity | 230 | 300 | 220 | 270 | 200 | 110 |
| Rate Constant [1] | 0.287 | 0.441 | 0.397 | 0.414, 0.447 | 0.199, 0.141, 0.160 | 0.240 |
| DiPB/Cumene [2] | 14.6 | 14.5 | 16.0 | 15.6, 17.0 | 16.1, 17.3, 17.1 | 12.2 |
| TriPB/Cumene [3] | 1.37 | 1.3 | 1.66 | 1.48, 1.85 | 1.61, 1.90, 1.88 | 1.22 |
| BET Surface Area, $m^2$/g | 389 | 379 | 390 | 394 | 435 | 342 |

[1] $2^{nd}$ order rate constant (k2) for alkylation of benzene with propylene.
[2] Weight Ratio at 3 hours time-on-stream × 100.
[3] Weight Ratio at 3 hours time-on-stream × 100.

$N_2$ stream for an additional 3 hours. The temperature was then raised to 534° C. at a rate of 28° C. per hour. The percentage of $O_2$ was gradually increased to 12.6% $O_2$, and the extrudate was held at 534° C. in 12.6% $O_2$ for 12 hours. The extrudate was then cooled to room temperature.

The catalyst comprising MCM-56 manufactured in this Example 6 was characterized by measuring the BET surface area, concentration of sodium as determined by inductively coupled plasma (ICP) by a commonly known method. Alpha Activity (hexane cracking) was determined as described in U.S. Pat. No. 3,354,078.

Examples 7, 8 and 9

Three additional catalysts were formulated as in Example 6, except that one comprised 60 wt. % MCM-56 and 40 wt. % alumina (Example 7), another comprised 80 wt. % MCM-56 and 20 wt. % alumina (Example 8), and another comprised 20 wt. % MCM-56 and 80 wt. % alumina (Example 9). The catalysts comprising MCM-56 manufactured in these Examples were characterized by measuring the BET surface area, concentration of sodium as determined by ICP, and Alpha Test activity (hexane cracking) as it is commonly known in the patent literature.

Example 10

To further test the catalysts of Examples 6, 7, 8 and 9, 0.5 gram of extrudate catalyst was loaded in a wire mesh screen basket along with 12 grams of quartz chips. The basket and contents were dried overnight (~16 hours) in an oven at 236° C. The basket was then loaded in a 300 cc Parr autoclave. The autoclave was sealed and purged free of air with flowing nitrogen. The autoclave was heated to 159° C. and purged with 100 sccm of nitrogen for 2 hours. The autoclave agitator was set to 500 rpm. Then, 156.1 grams of benzene was transferred to the autoclave, and the temperature was set to 125° C. at an agitation speed of 500 rpm for 1 hour. After 1 hour, 28.1 grams of propylene was transferred to the autoclave using a 75 cc Hoke transfer vessel. A constant All patents, patent applications, test procedures, priority documents, articles, is publications, manuals, and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

While the illustrative embodiments of the invention have been described with particularity, it will be understood that various other modifications will be apparent to and may be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

We claim:

1. A method for manufacturing synthetic porous crystalline MCM-56 material comprising the steps of:
  a) preparing a first reaction mixture containing sources of alkali or alkaline earth metal (M) cation, an oxide of a trivalent element X, an oxide of a tetravalent element Y, zeolite seed crystals, and water, said first reaction mixture having a composition in terms of mole ratios of oxides within the following ranges:
  $YO_2/X_2O_3$=5 to 35;
  $H_2O/YO_2$=10 to 70;
  $OH^-/YO_2$=0.05 to 0.20;
  $M/YO_2$=0.05 to 3.0;
  said first reaction mixture further comprising zeolite seed crystals in an amount from greater than or equal to 0.05 wt. % to less than or equal to 5 wt. %, based on the weight of said first reaction mixture;
  b) adding directing agent R to the reaction mixture of step a) to form a second reaction mixture, having said directing agent R in terms of a mole ratio within the following range: $R/YO_2$=0.08 to 0.3; and c) crystallizing said second reaction mixture of step b) under conditions of temperature of from about 90° C. to about 175° C. and a time for less than 90 hours to form a resulting mixture comprising crystals of said MCM-56 material and less than 10 wt. % non-MCM-56 impurity crystals based on the total weight of said MCM-56 crystals in said second reaction mixture, as identified by X-ray diffraction, wherein said crystals of said MCM-56 material have an X-ray diffraction pattern as shown in Table 1:

TABLE 1

| Interplanar d-Spacing (Angstroms) | Relative Intensity |
|---|---|
| 12.4 ± 0.2 | vs |
| 9.9 ± 0.3 | m |
| 6.9 ± 0.1 | w |
| 6.4 ± 0.3 | w |
| 6.2 ± 0.1 | w |
| 3.57 ± 0.07 | m-s |
| 3.44 ± 0.07 | vs. |

2. The method of claim 1, wherein said amount of said zeolite seed crystals in said first reaction mixture is in the range of greater than or equal to 0.10 wt. % to less than or equal to 3 wt. %, based on the weight of the first reaction mixture.

3. The method of claim 1, wherein said directing agent R is selected from the group consisting of cyclopentylamine, cyclohexylamine, cycloheptylamine, hexamethyleneimine (HMI), heptamethyleneimine, homopiperazine, and combinations thereof.

4. The method of claim 1, wherein said directing agent R comprises hexamethyleneimine (HMI), X comprises aluminum and Y comprises silicon.

5. The method of claim 1, wherein said resulting mixture of step c) comprises less than or equal to about 5 wt. % non-MCM-56 impurity crystals, based on the total weight of said MCM-56 crystals in said second reaction mixture, as identified by X-ray diffraction.

6. The method of claim 1, wherein said first reaction mixture has a composition in terms of mole ratios of oxides within the following ranges:

$YO_2/X_2O_3$=15 to 20;
$H_2O/YO_2$=15 to 20;
$OH^-/YO_2$=0.1 to 0.15;
$M/YO_2$=0.11 to 0.15;

said first reaction mixture further comprising zeolite seed crystals in an amount from greater than or equal to 1 wt. % to less than or equal to 3 wt. %, based on the weight of said first reaction mixture; and step b) comprises adding hexamethyleneimine (HMI) as said directing agent R to said first reaction mixture to form a second reaction mixture having HMI in terms of a mole ratio within the range of: $HMI/YO_2$=0.1 to 0.2.

7. The method of claim 1, wherein said conditions of crystallizing step c) include crystallizing said second reaction mixture for less than 40 hours.

8. The method of claim 1, wherein said conditions of crystallizing step c) include a temperature of from about 125° C. to about 175° C. for from about 20 to about 75 hours.

9. The method of claim 1, wherein said second reaction mixture of step b) has a solids content of less than 30 wt. % based on the weight of said second reaction mixture.

10. The method of claim 1, wherein said zeolite seed crystals exhibit the X-ray diffraction pattern for an MCM-22 family material.

11. The method of claim 1, wherein said zeolite seed crystals exhibit said X-ray diffraction pattern for said MCM-56 crystals as set forth in Table 1.

12. The method of claim 1, wherein said second reaction mixture of step b) is aged prior to crystallizing step c) for from about 0.5 to about 48 hours at a temperature of from about 25 to about 75° C.

13. The method of claim 1, further comprising the step of:

d) separating and recovering at least a portion of said crystals of said MCM-56 material from said resulting mixture of step c), wherein said crystals of MCM-56 from step d) are thermally treated by heating at a temperature of from about 370° C. to about 925° C. for a time of from 1 minute to about 20 hours to form calcined MCM-56 crystals, wherein said calcined MCM-56 crystals have an X-ray diffraction pattern as shown in Table 2:

TABLE 2

| Interplanar d-Spacing (Angstroms) | Relative Intensity |
|---|---|
| 12.4 ± 0.2 | vs |
| 9.9 ± 0.3 | m |
| 6.9 ± 0.1 | w |
| 6.2 ± 0.1 | s |
| 3.55 ± 0.07 | m-s |
| 3.42 ± 0.07 | vs. |

14. The method of claim 1, wherein said non-MCM-56 impurity crystal is selected from the group consisting of MCM-22, MCM-49, ITQ-1, ITQ-2, PSH-3, SSZ-25, ERB-1, UZM-8 and UZM-8HS and mixtures thereof.

15. The method of claim 1, wherein said non-MCM-56 impurity crystal is selected from the group consisting of ferrierite, kenyaite and mixtures thereof.

* * * * *